United States Patent [19]

Komai et al.

[11] 4,119,657
[45] Oct. 10, 1978

[54] NOVEL PEROXYCARBONATE

[75] Inventors: Takeshi Komai, Aichi; Kazuo Matsuyama, Gamagori, both of Japan

[73] Assignee: Nihon Oil and Fats Co., Ltd., Tokyo, Japan

[21] Appl. No.: 798,846

[22] Filed: May 20, 1977

[30] Foreign Application Priority Data

Jun. 16, 1976 [JP] Japan .................................. 51/69720

[51] Int. Cl.² .............................................. C07C 69/02
[52] U.S. Cl. .............................. 260/453 RZ; 526/319
[58] Field of Search .................................. 260/453 RZ

[56] References Cited

U.S. PATENT DOCUMENTS

| 2,374,789 | 5/1945 | Strain .......................... 260/453 RZ |
| 2,567,615 | 9/1951 | Milas ........................... 260/453 RZ |
| 3,082,236 | 3/1963 | Mageli et al. ................. 260/453 RZ |
| 3,326,859 | 6/1967 | Seiner .......................... 260/453 RZ |

FOREIGN PATENT DOCUMENTS

1,041,088  9/1964  United Kingdom.

*Primary Examiner*—Lewis Gotts
*Assistant Examiner*—Robert C. Whittenbaugh
*Attorney, Agent, or Firm*—Blanchard, Flynn, Thiel, Boutell & Tanis

[57] ABSTRACT

Peroxycarbonates having the following formula are copolymerizable with non-conjugated ethylenically unsaturated monomers and have good storage stability,

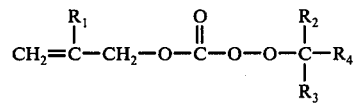

in which $R_1$ represents a hydrogen atom or a lower alkyl group having one to four carbon atoms, $R_2$ and $R_3$ represent lower alkyl groups having one to four carbon atoms, and $R_4$ represents an alkyl group having one to 12 carbon atoms or a cyclo alkyl group having three to 12 carbon atoms.

7 Claims, No Drawings

NOVEL PEROXYCARBONATE

BACKGROUND OF THE INVENTION

1. Field of the Invention

This invention relates to a peroxide having a polymerizable double bond and a peroxide group in the molecule and more particularly to a novel peroxycarbonate which possesses excellent copolymerizability with non-conjugated ethylenically unsaturated monomers.

2. Description of the Prior Art

Heretofore, there have been known some peroxides having a polymerizable double bond. For example British Pat. No. 1,041,088 discloses that t-butyl peroxymethacrylate is copolymerized with methyl methacrylate whereby a copolymer having a peroxyester group is obtained and that the said copolymer is subjected to graft copolymerization.

Japanese Patent Publication No. SHO46-34100 discloses that di(t-butylperoxy) fumarate is copolymerized with styrene whereby there is obtained a copolymer having a peroxyester group and the said copolymer is subjected to graft copolymerization with methyl acrylate.

Japanese Patent Publication No. SHO38-5972 discloses that t-butyl peroxycrotonate is copolymerized with vinyl chloride to obtain a copolymer having a peroxyester group and the thus obtained copolymer is mixed with a natural rubber latex at high temperature whereby blended polymers are obtained.

Japanese Patent Publication No. SHO44-21721 discloses that resins which possess good extrusion properties and transparency are obtained by polymerization of ethylene using t-butyl peroxyvinylacetate.

As mentioned above, the peroxyesters having a polymerizable double bond are superior to the peroxyesters which do not contain a double bond in many points but the former peroxyesters also have some defects.

For example such compounds which self-polymerize easily such as butyl peroxymethacrylate as well as the acid chloride thereof, which are the starting materials therefor are not stable during storage and are inconvenient to handle.

Further, as the said peroxides are conjugated monomers, they are high in copolymerization reactivity with conjugated monomers having a Alfrey-Price value of 0.2 or above such as styrene, butadiene, methyl acrylate and methyl methacrylate but they are low in copolymerization reactivity with non-conjugated monomers having a Alfrey-Price value of lower than 0.2 such as vinyl acetate, vinyl chloride and di-allylphthalate [Refer to High Molecular Chemical Association: Copolymerization No. 1 Reaction Analysis (Baifukan) page 89]. As a result they are not suitable for copolymerization with the non-conjugated monomers.

Further, a compound which possesses high copolymerization reactivity such as di(t-butylperoxy)fumarate can not distribute the peroxyester groups in the polymer uniformly in a broad range of the concentration thereof.

Especially, when the concentration of the peroxyester groups is small, the peroxyester groups become present locally in the polymer with the result being that graft copolymers having good properties can not be obtained.

Furthermore, t-butylperoxycrotonate, because its peroxy group in the copolymer obtained by the copolymerization is a peroxyester of a secondary carboxylic acid, is active at low temperature and thus it is unsuitable for use as a free radical initiator at high temperature.

SUMMARY OF THE INVENTION

It is an object of the present invention to provide new peroxycarbonates.

It is another object of the present invention to provide a process for producing new peroxycarbonates.

It is still another object of the present invention to provide peroxycarbonates having splendid copolymerization ability with a non-conjugated ethylenically unsaturated monomer.

It is still a further object of the present invention to provide peroxycarbonates having good storage stability.

The peroxycarbonates of the present invention have the following general formula.

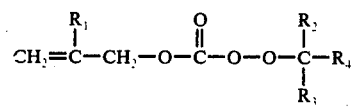

In which $R_1$ represents a hydrogen atom or a lower alkyl group having one to four carbon atoms, $R_2$ and $R_3$ represent lower alkyl groups having one to four carbon atoms, and $R_4$ represents an alkyl group having one to 12 carbon atoms or a cyclo alkyl group having three to 12 carbon atoms.

Illustrative peroxycarbonates are t-butylperoxy allyl carbonate, t-hexylperoxy allyl carbonate, 1,1,3,3-tetramethylbutylperoxy allyl carbonate, p-menthaneperoxy allyl carbonate, t-butylperoxy methallyl carbonate, t-hexylperoxy methallyl carbonate, 1,1,3,3-tetramethylbutylperoxy methallyl carbonate, p-methaneperoxy methallyl carbonate and the like.

The peroxycarbonate of the present invention is identified by establishing the presence of the peroxycarbonate group and the unsaturated double bond in the molecule from the infrared absorption spectrum thereof and by establishing the structure of the alkyl or cycloalkyl group from the nuclear magnetic resonance spectrum group thereof, whereby the structural formula thereof is determined. The purity of the peroxycarbonate can be obtained from the amount of active oxygen in the compound.

The susceptibility of the peroxycarbonate to heat decomposition can be ascertained from its half life and the foaming temperature thereof.

Identification of the respective peroxycarbonates and some properties of the same are shown in Table 1 and the following examples. The peroxycarbonates of the present invention are obtained by reacting allyl chloroformate or methallyl chloroformate with tertiary alkyl hydroperexide or by reacting tertiary alkylperoxy chloroformate with allyl alcohol or methallyl alcohol in the presence of alkalis or tertiary amines.

The half-lives of the representative peroxycarbonates of the present invention and of comparative peroxides are shown in Table 1. From this Table, it was recognized that the peroxycarbonates of the present invention possess as much decomposition activity as t-butylperoxy isopropyl carbonate, which is a conventional polymerization initiator, and that the half-life of the copolymer of t-butylperoxy allyl carbonate or methallyl carbonate with diallyl phthalate is nearly the same as that of the peroxide before the polymerization process and that it is more active at elevated temperature than t-butyl peroxyisobutyrate which is a peroxyester of a secondary carboxylic acid.

Further, the peroxycarbonates of the present invention are stable notwithstanding the fact that they contain a double bond and deteriorate a little while they are left standing at room temperature for several months.

Then, it was recognized that they possess almost the same storage stability as t-alkylperoxy isopropyl carbonate.

The peroxycarbonate of the present invention is copolymerizable with other ethylenically unsaturated monomers under the condition wherein the peroxide bond is not broken, thereby to obtain a copolymer containing the peroxycarbonate group.

Table 1.

Half lives of peroxides at 105° C

|  | Peroxide | Solvent | Half life (hours) |
|---|---|---|---|
| This Invention | t-butylperoxy allyl carbonate | benzene / toluene | 3.9 / 6.9 |
|  | t-hexylperoxy allyl carbonate | benzene | 3.8 |
|  | 1,1,3,3-tetramethyl-butylperoxy allyl carbonate | benzene | 1.4 |
|  | t-butylperoxy methallyl carbonate | benzene / toluene | 2.9 / 4.9 |
|  | t-hexylperoxy methallyl carbonate | benzene | 2.9 |
|  | 1,1,3,3-tetramethyl-peroxy methallyl carbonate | benzene | 1.1 |
| Comparative example | t-butylperoxy isopropyl carbonate | benzene | 4.1 |
|  | copolymer of t-butylperpoxy allyl carbonate and diallyl phthalate (3:97) | benzene | 7.0 |
|  | copolymer of t-butylperoxy-methallyl carbonate and diallyl phthalate (2:98) | benzene | 6.4 |
|  | t-butyl peroxy isobutyrate | benzene | 0.37 |

The content of the peroxide constituent in the thus obtained copolymer (copolymerization ratio of peroxide) depends upon the charging ratio of the respective components used, and the copolymerization process.

Accordingly, the copolymer having the desired copolymerization ratio of the components can be obtained when the above mentioned factors as a parameter of the said ratio are adjusted.

As the content of the peroxycarbonate in the copolymer is especially affected by the copolymerization temperature, it is preferable that the copolymerization is carried out under the conditions wherein the peroxy bonds are not broken, for example at a copolymerization temperature of under 100° C, preferably 10°–90° C.

Illustrative free radical polymerization initiators which can be used effectively are, for example, acetyl cyclohexylsulfonyl peroxide, isobutyryl peroxide, diisopropyl peroxydicarbonate, t-butyl peroxypivalate, lauroyl peroxide, benzoyl peroxide, t-butyl peroxyisobutyrate, 1,1-bis (t-butylperoxy) 3,3,5-trimethylcyclohexane, persulfate and the like.

The copolymerization using the peroxycarbonate of the present invention can be carried out by a vinyl polymerization method using a free radical which has been known as a polymerization initiator, that is to say, a bulk polymerization, a solution polymerization, or a water soluble medium polymerization.

It is necessary for distributing the peroxide groups uniformly in the copolymers to select an adequate ethylenically unsaturated monomer.

As for the ethylenically unsaturated monomers, non-conjugated monomers having the beforementioned Alfrey-Price value of lower than 0.2, for example, α-olefine such as ethylene and propylene, vinyl esters of inorganic acids such as vinyl chloride and vinyl bromide; vinyl esters of monocarboxylic acids such as vinyl acetate, vinyl benzoate, vinyl valerate and vinyl caproate, vinyl ester of polycarboxylic acid such as divinyl succinate: divinyl adipate, vinyl allyl phthalate, vinyl methallyl pimelate and vinyl methyl glutarate; vinyl ethers such as vinyl ethyl ether, vinyl butyl ether and vinyl allyl ether; vinyl ketones such as vinyl butyl ketone and vinyl ethyl ketone; allyl derivatives such as allyl acetate, allyl butyrate, diallyl phthalate, allyl chloride, diallyl adipate and methallyl propionate are preferable.

However, conjugated monomers having an Alfrey-Price value of 0.2, or above for example, styrene derivatives such as styrene, α-methylstyrene, dichlorostyrene, vinylnaphthalene, and vinyl phenol; acrylic acid esters of and α-alkylsubstituted acrylic acid; unsaturated acid such as methyl acrylate, methyl methacrylate, ethyl acrylate, and butyl acrylate; vinylidene halides such as vinylidene chloride, vinylidene bromide and vinylidene fluoride; vinyl esters of hydrocyanic acid such as acrylonitrile and methacrylonitrile; unsaturated vinyl and allylesters such as vinyl acrylate, vinyl methacrylate, allyl acrylate and allyl methacrylate, conjugated dienes such as butadiene, isoprene and chloroprene can be used.

A copolymer in which the peroxide groups are distributed uniformly, can be effectively subjected to curing, chemical cross-linking, or graft copolymerization and it is a very important intermediate for industrial use.

PREFERRED EMBODIMENTS OF THE INVENTION

EXAMPLE 1

Production of t-butylperoxy allyl carbonate 13.3g(0.33 mole) of sodium hydroxide was dissolved into 119.7g of water to form 10 wt % aqueous solution of sodium hydroxide, into which 33.0g (0.30 mol) of t-butyl hydroperoxide (purity 82 %) was added little by little at a temperature of under 20° C with stirring. To the resultant solution 36.5 g (0.30 mol) of 100% purity of allyl chloroformate was added little by little for 20 minutes at a temperature of 10° C.

After the adding operations were completed, the resultant solution was allowed to continue reaction with stirring for 1 hour with the temperature kept at 15° C until the reaction was completed. After the aqueous layer was separated, the organic layer was washed at 20° C once with 30 g of 10 wt % an aqueous solution of sodium hydroxide, and once with 30 g of an aqueous solution of 10 wt % of sodium sulfate and then was washed once with 30 g of a buffer solution consisting of 6 wt % of acetic acid, 6 wt % of sodium sulfite and water and was further washed twice with 30 g of an aqueous solution of 10 wt % of sodium sulfate. The obtained organic layer was dried with 5 g of magnesium sulfate, whereby 41.0 g of t-butylperoxy allyl carbonate which was in a liquid state at room temperature, was obtained. (yield: 73.5 %).

The amount of active oxygen was 8.60 % (theoretical value : 9.18 % purity : 93.7 ) and the foaming decomposition temperature was 117.5° C.

The characteristic absorptions in the infrared spectrum of this compound occurred at 1787 cm$^{-1}$ ($\nu$ c=o), 1767 cm$^{-1}$ ($\nu$ c=o) and 1648 cm$^{-1}$ ($\nu$ c=c). The results of the nuclear magnetic resonance spectrum showed that when a chemical shift of a proton was shown as $\tau$ value, the peak of the proton of =CH — group was observed at 3.0, the proton of H$_2$C=C group at 3.6, the proton of —CH$_2$O — group at 4.2 and the proton of t-butyl group at 8.6.

From these results, the obtained compound was recognized to be t-butylperoxy allyl carbonate.

EXAMPLE 2

Production of t-hexylperoxy allyl carbonate

The reaction was carried out according to the same procedure as that described in Example 1 except that 38.1 g of t-hexyl hydroperoxide of purity 93 % was used in place of t-butyl hydroperoxide, whereby 47.9 g of t-hexylperoxy allyl carbonate (yield 73.3 %) was obtained.

The obtained compound was liquid at room temperature and the amount of active oxygen was 7.34 % (theoretical value : 7.91 %, purity 92.8 %). The foaming decomposition temperature was 107.3° C.

The characteristic absorption in the infrared spectrum of the compound occurred at 1787 cm$^{-1}$ ($\nu$ c=o), 1767 cm$^{-1}$ ($\nu$ c=o) and 1648 cm$^{-1}$ ($\nu$ c=c). Showing the chemical shifts of the protons as the value of $\tau$ in the nuclear magnetic resonance spectrum, the peak for the proton of =CH — group was observed at 3.0, that of H$_2$C= group at 3.6, that of —CH$_2$O — group at 4.2 and that of t-hexyl group at 8.48, 8.72 and 9.06. From these results, the obtained compound was recognized to be t-hexylperoxy allyl carbonate.

EXAMPLE 3

Production of 1,1,3,3-tetramethylbutylperoxy allyl carbonate 6.0 g (0.11 mole) of sodium hydroxide was dissolved into 24.0 g of water to obtain 20 wt % aqueous solution of sodium hydroxide, into which 14.6 g of 1,1,3,3-tetramethylbutyl hydroperoxide (purity : 96%) was added little by little at a temperature of under 20° C. Into the resultant solution 13.5 g (0.11 mole) of 100 % purity of allyl chloroformate was dropped little by little for 10 minutes at a temperature of 15° C. After the dropping procedures were completed, the resultant solution was allowed to continue the reaction with the temperature kept at 15° C for one hour until the reaction was completed.

After the aqueous layer was separated, the organic layer of the resultant reaction solution was washed once at 10° C with 50 g of 10 wt % aqueous solution of sodium hydroxide, and twice with 50 g of 10 wt % aqueous solution of sodium sulfate and then once with 50 g of a buffer solution consisting of 10 wt % of sodium acetate, 6 wt % of acetic acid, 6 wt % of sodium sulfite and water, and further once with 50 g of 10 wt % aqueous solution of sodium sulfate. The thus purified organic layer was dried with magnesium sulfate to obtain 14.6 g of 1,1,3,3-tetramethylbutylperoxy allyl carbonate which is liquid at room temperature (yield: 56.0 %).

The amount of active oxygen was 6.93 % (theoretical value: 6.96 %, purity: 99.6 %) and the foaming decomposition temperature was 103.5° C.

The characteristic absorption in the infrared spectrum of this compound were observed at 1787 cm$^{-1}$ ($\nu$ c=o), 1767 cm$^{-1}$ ($\nu$ c=o) and 1648 cm$^{-1}$ ($\nu$ c=c). When the chemical shifts of the protons in the nuclear magnetic resonance spectrum were shown as the value of $\tau$, the peak of the proton of =CH — group was observed at 3.0, that of H$_2$C = group at 3.6, that of —CH$_2$O — group at 4.2, and those of 1,1,3,3-tetramethylbutyl group were observed at 8.36, 8.62 and 8.96.

From these results, the obtained product was confirmed to be 1,1,3,3-tetramethylbutylperoxy allyl carbonate.

EXAMPLE 4

Production of t-butylperoxy methallyl carbonate

Into 10 wt % aqueous solution of sodium hydroxide obtained by dissolving 12.9 g (0.32 mole) of sodium hydroxide into 116.1 g of water, 33.3 g (0.30 mole) of t-butyl hydroperoxide (purity : 81 %) was added little by little at a temperature of under 20° C with stirring.

42.5 g (0.30 mole) of 95 % methallyl chloroformate was dropped little by little into the resultant solution of 10 minutes. After the dropping procedures were completed, the obtained reaction solution was allowed to continue the reaction with the temperature kept at 15° C for 3 hours.

After the aqueous layer was separated, the organic layer of the reaction solution was washed once with 74 g of 10 wt % aqueous solution of sodium hydroxide at 10° C, then once with 75 g of 10 wt % aqueous solution of sodium sulfate, further once with 75 g of a buffer solution consisting of 10 wt % of sodium acetate, 6 wt % of acetic acid, 6 wt % of sodium sulfite and water, and still further twice with 75 g of 10 wt % aqueous solution of sodium sulfate.

The resultant purified organic layer was dried with magnesium sulfate, whereby 43.5 g of t-butylperoxy methallyl carbonate was obtained with the yield of 73.3 %.

The amount of active oxygen was 8.09 % (theoretical value ; 8.61 % purity ; 95.1 %).

The foaming temperature was 117.5° C. The characteristic absorptions of this compound in the infrared absorption spectrum were observed at 1788 cm$^{-1}$ ($\nu$ c=o), 1767 cm$^{-1}$ ($\nu$ c=o), and 1657 cm$^{-1}$ ($\nu$ c=c).

When the chemical shift of the proton was shown as the value of $\tau$, the peak of the proton of H$_2$C = group was observed at 5.42, that of —CH$_2$O — group at 5.42, that of

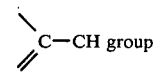

at 8.20 and that of t - butyl group was observed at 9.70. From these results, the obtained compound was confirmed to be t -butylperoxy methallyl carbonate.

EXAMPLE 5

Production of t-hexylperoxy methallyl carbonate

The reaction was carried out according to the same procedure as that described in Example 4 except that 93% t-hexyl hydroperoxide was used in place of t-butyl hydroperoxide, whereby 52.2 g of t-hexylperoxyme-thallyl carbonate which was liquid at room temperature, was obtained with the yield of 75.6 %. The amount of active oxygen was 6.96 % (the theoretical value of the active oxygen ; 7.41 %, the purity was 93.9 %) the foaming temperature of this compound was 115.5° C. The characterisitc absorptions of this compound in the infrared spectrum were observed at 1788 cm$^{-1}$ ($\nu$ c=o), 1767 cm$^{-1}$ ($\nu$ c=c), and 1657 cm$^{-1}$ ($\nu$ c=c).

When the chemical shift of the proton in the nuclear magnetic resonance spectrum was shown as the value of $\tau$, the peak of the proton of H$_2$C= group was observed at 5.00, that of — CH$_2$O — group at 5.42, that of

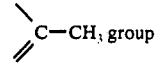

at 8.20 and those of t-hexyl group were observed at 8.48, 8.72 and 9.06. From these results, the obtained compound was recognized to be t-hexylperoxy methallyl carbonate.

EXAMPLE 6

Production of 1,1,3,3-tetramethylbutylperoxy methallyl carbonate

Into 10 wt % aqueous solution of sodium hydroxide obtained by dissolving 8.6 g (0.22 mole) of sodium hydroxide into 77.4 g of water, 48.7 g (0.20 mole) of 1,1,3,3-tetramethylbutyl hydroperoxide (purity : 60 %) was added little by little at a temperature of under 20° C with stirring.

Then 28.5 g (0.20 mole) of 95 % methallyl choloformate was added into the resultant solution for about 15 minutes at a temperature of 15° C. After the adding procedures were finished, the resultant reaction solution was allowed to continue the reaction for 3 hours with the temperature kept at 15° C. After the aqueous layer was separated, the organic layer of the resultant reaction solution was washed once at 10° C with 100 g of 10 wt % aqueous solution of sodium hydroxide, then once with 100 g of 10 wt % aqueous solution of sodium sulfate, further once with 100 g of a Buffer solution consisting of 10 wt % of sodium acetate, 6 wt % of acetic acid, 6 wt % of sodium sulfite and water, and still further it was washed twice with 10 wt % aqueous solution of sodium sulfate.

The resultant purified organic layer was dried with magnesium sulfate, whereby 47.1 g of 1,1,3,3-tetramethylbutylperoxy methallyl carbonate which was liquid at room temperature, was obtained with the yield of 72.9 %.

The amount of active oxygen was 4.95 % (the theoretical value of active oxygen is 6.56 %, then its purity is 75.5 %). The foaming temperature was 106.5° C.

The characteristic absorptions of this compound in the infrared spectrum were observed at 1788 cm$^{-1}$ ($\nu$ c=o), 1767 cm$^{-1}$ ($\nu$ c=o), and 1657$^{-1}$ ($\nu$ c=C). When the chemical shift of the proton in the nuclear magnetic resonance spectrum was shown as the value of $\tau$, the peak of the proton of H$_2$C=group was observed at 5.00, that of — CH$_2$O — group at 5.42, that of $$\diagdown\!\!\!\!\!\underset{/\!\!\!\!/}{C}\!\!-\!\!CH_3 \text{ group}$$

at 8.20 and those of 1,1,3,3-tetramethylbutyl group were observed at 8.35, 8.62 and 8.96.

From these results, the obtained product was confirmed to be 1,1,3,3-tetramethylbutylperoxy methallyl carbonate.

COPOLYMERIZATION OF PEROXYCARBONATE

REFERENCE EXAMPLES 1 - 6

Copolymerization of t-butylperoxy allyl carbonate with diallyl phthalate

The respective weights of 94 % t-butylperoxyallyl carbonate (hereinafter described as TBPA), 100 % diallyl phthalate (hereinafter described as DAP) and 99 % diisopropyl peroxydicarbonate (hereinafter described as lPP) as shown in Table 2 were charged into respective ampules.

The atmospheres in the respective ampules were substituted with nitrogen gas and the ampules were sealed. Then, the resultant reaction mixture was subjected to bulk copolymerization at 50°C for 5 hours. The reaction product was cooled and then was dropped into 250 ml of methanol.

The resultant precipitate was filtered off and was dried. After the drying procedure was finished, the obtained product was weighed to calculate the copolymerization rate.

Further, the amount of active oxygen of the respective obtained copolymer was measured by iodometry and the copolymerization ratio of the respective copolymer was estimated from the nuclear magnetic resonance spectrum thereof.

The obtained results are shown in Table 2. It was clarified from Table 2 that the larger is the amount of charging ratio of TBPA, the larger is the amount of active oxygen of the copolymer.

It was recognized that the peroxycarbonate of the present invention is suitable for copolymerization with DAP.

Table 2.

| | Copolymerization of t-butylperoxyallylcarbonate with diallyl phthalate | | | | | |
|---|---|---|---|---|---|---|
| | Reference example | 1 | 2 | 3 | 4 | 5 |
| Charging Composition | Weight of TBPA (g) | 0.63 | 1.27 | 2.53 | 5.04 | 9.03 |
| | Weight of DAP (g) | 15.15 | 14.57 | 14.15 | 10.93 | 5.82 |
| | Weight of IPP (g) | 0.17 0.17 | 0.17 | 0.15 | 0.17 | |
| | Charging ratio of TBPA/DAP* | 0.04/ 1.10 | 0.08/ 1.00 | 0.17/ 1.00 | 0.43/ 1.00 | 1.45/ 1.00 |
| | Copolymerization time (hours) | 5.0 | 5.0 | 5.0 | 5.0 | 5.0 |
| Copolymer | Copolymerization rate (%) | 11.5 | 10.2 | 8.8 | 5.4 | 3.6 |
| | amount of active oxygen (%) | 0.22 | 0.33 | 0.70 | 1.54 | 3.14 |
| | Copolymerization ratio of TBPA/DAP* | 0.02/ 1.00 | 0.04/ 1.00 | 0.08/ 1.00 | 0.20/ 1.00 | 0.51/ 1.00 |

*TBPA was calculated as 100% of TBPA

REFERENCE EXAMPLE 6 – 9.

Copolymerization of t-butylperoxy methallyl carbonate with diallyl phthalate

The copolymerization was carried out according to the same procedure as that described in reference examples 1 – 5 except that 90 % t-butylperoxy methallyl carbonate (hereinafter described as TBPM) was used in place of TBTA), with the charging component as shown in Table 3.

Table 3.

Copolymerization of t-butylperoxy methallyl carbonate with diallyl phthalate

| | Reference example | 6 | 7 | 8 | 9 |
|---|---|---|---|---|---|
| Charging Composition | Weight of TBPM (g) | 2.89 | 4.86 | 7.75 | 10.67 |
| | Weight of DAP (g) | 12.91 | 10.61 | 7.37 | 4.09 |
| | Weight of IPP (g) | 0.21 | 0.21 | 0.21 | 0.21 |
| | Charging ratio of TBPM/DAP* | 0.20/1.00 | 0.41/1.00 | 0.94/1.00 | 2.34/1.00 |
| | Copolymerization time (hours) | 6.0 | 9.0 | 18.0 | 26.0 |
| Copolymer | Copolymerization rate (%) | 4.6 | 3.5 | 6.6 | 1.4 |
| | Copolymerization ratio of TBPM/DAP* | 0.06/1.00 | 0.11/1.00 | 0.23/1.00 | 0.60/1.00 |

*TBPM was calculated as 100% of TBPM

It was obtained from table 3 that the larger is the charging ratio of TBPM the larger is the copolymerization ratio thereof, and accordingly peroxycarbonates of the present invention are suitable for copolymerization with DAP.

REFERENCE EXAMPLE 10 – 14

Copolymerization of t-butylperoxy allyl carbonate with vinyl acetate

The copolymerization was carried out according to the same procedure as that described in reference example 1 – 5 except that 100 % vinyl acetate (hereinafter described as VAC) and petroleum ether were used in place of DAP and methanol. The charging component, the copolymerization time and the obtained results are shown in Table 4. The limiting viscosity number was measured in benzene at 30° C.

Table 4

Copolymerization of t-butylperoxy allyl carbonate with vinyl acetate

| | Reference Example | 10 | 11 | 12 | 13 | 14 |
|---|---|---|---|---|---|---|
| Charging composition | Weight of TBPA (g) | 1.47 | 4.92 | 7.90 | 10.38 | 13.31 |
| | Weight of VAC (g) | 12.50 | 9.22 | 6.89 | 4.12 | 1.55 |
| | Weight of IPP (g) | 0.10 | 0.09 | 0.09 | 0.10 | 0.10 |
| | Charging ratio of TBPA/VAC* | 0.11/1.00 | 0.50/1.00 | 1.08/1.00 | 2.37/1.00 | 8.08/1.00 |
| | Copolymerization time (hours) | 2 | 10 | 40 | 40 | 480 |
| Copolymer | Copolymerization rate (%) | 2.7 | 3.6 | 15.2 | 4.3 | 15.6 |
| | Amount of active oxygen (%) | 1.21 | 3.28 | 4.73 | 5.92 | 6.84 |
| | Copolymerization rate of TBPA/VAC | 0.13/1.00 | 0.64/1.00 | 1.04/1.00 | 2.11/1.00 | 6.41/1.00 |
| | Limiting viscosity number | 0.30 | 0.11 | 0.07 | 0.04 | 0.03 |

*TBPA was calculated as 100% of TBPA

From table 4, it was recognized that the more the charging ratio of TBPA is increased the larger is the amount of active oxygen in the copolymer and further the larger is the copolymerization ratio of TBPA and accordingly the peroxycarbonates of the present invention are suitable for copolymerization with vinyl acetate.

REFERENCE EXAMPLE 15 – 19

Copolymerization of t-butylperoxy allyl carbonate with vinyl chloride.

The weights of 96 – 97 % TBPA, 100 % vinyl chloride (hereinafter described as VCL), IPP (used as 20 wt % toluene solution of IPP) and 100 ml of 0.2 wt % aqueous solution of polyvinyl alcohol (saponification value : 89%) as shown in Table 5 were charged into autoclaves respectively.

After the atmosphere in the respective autoclave was substituted with nitrogen gas, the respective resultant mixture was subjected to suspension copolymerization at 50° C for the number of hours as shown in Table 5.

The resultant reaction product was dropped into 300 ml of methanol and the obtained precipitate was filtered off and then was dried. After the drying procedure was completed, the thus obtained product was weighed and the copolymerization rate was calculated from the weight.

Further the amount of active oxygen of the respective obtained copolymer was measured by iodometry and the copolymerization ratio of the respective copolymer was estimated from the nuclear magnetic resonance spectrum thereof.

The limiting viscosity number of the respective copolymer was measured in tetrahydrofuran at 20° C.

The obtained results are shown in Table 5.

It was obtained from Table 5 that the larger is the charging ratio of TBPA, the larger is the amount of active oxygen of the copolymer and further the more the copolymerization ratio of TBPA is increased. From these facts, it was recognized that the peroxycarbonates of the present invention were suitable for copolymerization with VCl.

Table 5.

Copolymerization of t-butylperoxy allyl carbonate with vinyl chloride

| | Reference Example | 15 | 16 | 17 | 18 | 19 |
|---|---|---|---|---|---|---|
| Charging composition | Weight of TBPA (g) | 2.81 | 7.20 | 13.78 | 17.57 | 20.89 |
| | Weight of VCL (g) | 24.52 | 19.03 | 14.34 | 9.55 | 4.11 |
| | Weight of IPP (g) | 0.31 | 0.31 | 0.30 | 0.30 | 1.01** |
| | Charging ratio of TBPA/VCL* | 0.11/1.00 | 0.36/1.00 | 83 0.92/1.00 | 1.76/1.00 | 4.86/1.00 |
| | Copolymerization time (hours) | 4.0 | 4.0 | 4.0 | 6.5 | 6.0 |
| Copolymer | Copolymerization rate (%) | 67.8 | 60.8 | 29.5 | 14.7 | 28.7 |
| | Amount of active oxygen (%) | 0.93 | 2.19 | 2.94 | 3.63 | 5.23 |
| | Copolymerization rate of TBPA/VCL* | 0.12/1.00 | 0.45/1.00 | 0.88/1.00 | 1.57/1.00 | 5.41/1.00 |

Table 5.-continued

Copolymerization of t-butylperoxy allyl carbonate with vinyl chloride

| Limiting viscosity number | 0.534 | 0.107 | 0.182 | 0.120 | 0.05 |

*TBPA was calculated as 100% of TBPA

**IPP was used as 50% toluene solution of the same

The embodiments of the invention in which an exclusive property or privilege as claimed are defined as follows;

1. A compound having the formula

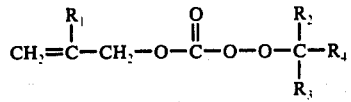

wherein $R_1$ is hydrogen or alkyl having 1 to 4 carbon atoms, $R_2$ and $R_3$ are alkyls having 1 to 4 carbon atoms, and $R_4$ is alkyl having 1 to 12 carbon atoms.

2. A compound as claimed in claim 1, t-butylperoxy allyl carbonate.

3. A compound as claimed in claim 1, t-hexylperoxy allyl carbonate.

4. A compound as claimed in claim 1, 1,1,3,3-tetramethylbutylperoxy allyl carbonate.

5. A compound as claimed in claim 1, t-butylperoxy methallyl carbonate.

6. A compound as claimed in claim 1, t-hexylperoxy methallyl carbonate.

7. A compound as claimed in claim 1, 1,1,3,3-tetramethylbutylperoxy methallyl carbonate.

* * * * *